US00PP36909P2

(12) United States Plant Patent
Espin

(10) Patent No.: US PP36,909 P2
(45) Date of Patent: Sep. 2, 2025

(54) GRAPEVINE PLANT NAMED 'BLOMG01'

(50) Latin Name: *Vitis vinifera*
Varietal Denomination: BLOMG01

(71) Applicant: BLOOM FRESH INTERNATIONAL LIMITED, London (GB)

(72) Inventor: Juan Carreño Espin, Murcia (ES)

(73) Assignee: BLOOM FRESH INTERNATIONAL LIMITED, London (GB)

( * ) Notice: Subject to any disclaimer, the term of this patent is extended or adjusted under 35 U.S.C. 154(b) by 0 days.

(21) Appl. No.: 18/989,662

(22) Filed: Dec. 20, 2024

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./207
CPC ..... A01H 5/08; A01H 5/00; A01H 6/88
See application file for complete search history.

(56) References Cited

U.S. PATENT DOCUMENTS

PP23,399 P2 * 2/2013 Cain ..... A01H 5/08
Plt./207

* cited by examiner

*Primary Examiner* — June Hwu
(74) *Attorney, Agent, or Firm* — Michael Best & Friedrich LLP

(57) ABSTRACT

'BLOMG01' is a new and distinct grapevine plant with novel characteristics that include good fertility and excellent fruity labrusca-toffee like flavor. The berries produced by 'BLOMG01' are yellowish green and seeded, with a very firm and crunchy texture. The berries produced by 'BLOMG01' are large, weighing 6.5 g/berry on average, and harvested in early July in Murcia Region (Spain).

1 Drawing Sheet

Latin name of the genus and species: *Vitis vinifera*.
Variety denomination: 'BLOMG01'.

BACKGROUND

Described herein is a new distinct variety of grapevine named 'BLOMG01'. The variety originated from a hybridization performed in Murcia, Spain during 2017 between 'Princess' (unpatented), as the pollen parent, and 'New York Muscat' (unpatented), as the seed parent. Abortive seed traces were embryo cultured and the resulting plant was planted in an evaluation block during 2018. The first evaluation of the fruit produced by 'BLOMG01' was performed during 2019. 'BLOMG01' was first asexually propagated by field grafting dormant hardwood scions to rootstock in 2020 in Murcia, Spain. Fruit from the resulting four grafted 'BLOMG01' vines was first harvested in 2021. All characteristics and distinctions remain true to form and are established and transmitted through succeeding propagations.

SUMMARY

The following are the most outstanding and distinguishing characteristics of 'BLOMG01'. 'BLOMG01' produces naturally large (6.5 g/berry), seeded, yellow green (2.5 GY 7/8) berries having a broad ellipsoid shape with an excellent unique fruity labrusca-toffee like flavor, very firm texture, and a high fertility index (1.3), that are harvested in early July, in Murcia, Spain.

'BLOMG01' is believed to be most similar to 'IFG Seven' (U.S. Plant Pat. No. 23,399). Nonetheless, the new cultivar can be distinguished from 'IFG Seven' based at least upon harvest period, berry shape, berry size and fertility index.

'BLOMG01' matures in early July while 'IFG Seven' matures in August-September. The berries produced by 'BLOMG01' have a broad ellipsoid shape while the berries produced by 'IFG Seven' have an elliptic-obtuse ovate shape, and the berries of 'BLOMG01' are smaller than the berries of 'IFG Seven' (6.5 g v. 9.7 g). 'BLOMG01' has a higher fertility index than 'IFG Seven' (1.3 v. 0.9-1.0).

'BLOMG01' can be distinguished from its male parent, 'Princess' (unpatented), in that the new cultivar has a harvesting time in early July, whereas 'Princess' has a harvest time in August-September. The berries of 'BLOMG01' have a labrusca-toffee like flavor while the berries of 'Princess' have a light muscat flavor. 'BLOMG01' has a higher fertility index than 'Princess' (1.3 v. 1.0).

'BLOMG01' can be distinguished from its female parent, 'New York Muscat' (unpatented), in that the new cultivar, 'BLOMG01', produces white (2.5GY7/8) colored grapes while 'New York Muscat' produces violet grapes. The berries of 'BLOMG01' have a firm texture whereas the berries of 'New York Muscat' have a soft texture. The berries of 'BLOMG01' have a labrusca-toffee like flavor while the berries of 'New York Muscat' have muscat flavor.

BRIEF DESCRIPTION OF THE DRAWINGS OR PHOTOGRAPHS

FIG. 1 shows the form, foliage, and fruit of a 3-year-old 'BLOMG01' grapevine plant grown in the field at Murcia, Spain. FIG. 1 shows, from the top in a clockwise direction: a cutting of a young shoot with tendrils and leaves, inflorescence, mature upper surface leaf, immature upper surface leaf, transverse sections of fruit, top view whole fruits, longitudinal section of fruit, side view of whole fruits, secondary fruit bunch and primary fruit bunch. The colors shown are as true as can be reasonably obtained by conventional photographic procedures.

DETAILED BOTANICAL DESCRIPTION

Throughout this specification, the color references are to the Munsell Plant Tissue Color Book, 2012 Edition by Munsell Color.

The following detailed description sets forth the distinctive characteristics of 'BLOMG01'. The detailed description was obtained between March and November using 3-year-old plants grown in the field in Murcia, Spain.

Classification:

*Family*.—Vitaceae.

*Botanical*.—*Vitis vinifera*.

*Common name*.—Grapevine.

*Cultivar name*.—'BLOMG01'.

Plant:

*Plant habit and growth*.—Semi-erect.

*Age at maturity*.—3 years old.

*Size* (*at maturity*).—Height — 225 cm. Width — 300 cm.

*Vigor*.—Medium.

*Productivity*.—High, 1.3 fertility index, around 6 pounds/plant and 12 Tn/acre.

*Rootstock*.—

*Name of rootstock*.—1103 Paulsen Rootstock (not patented).

*Age of rootstock at time of grafting*.—One year old.

Trunk:

*Size*.—Diameter — 5.325 cm. Height (at measured diameter of 4 cm) — 45 cm above the ground.

*Shape*.—Straight and cylindrical.

*Surface texture*.—Smooth, thin strips of peeling.

*Bark color*.—Interior — 5YR5/4. Exterior — 5YR4/4.

Canes:

*Size*.—Diameter — 8.31 mm. Length — 170 cm.

*Surface texture*.—Mature cane — smooth. Immature cane — smooth, slightly ribbed, with low density of prostate hairs on internodes.

*Form* (*woody shoot cross section form*).—Circular; pith in center with diaphragm at nodes.

*Color*.—Mature — 5 months, 5GY6/6 (anthocyanin 5YR4/4). Immature — 4 weeks, 2.5GY6/6 (anthocyanin 10R5/6). Dorsal side of internodes — 5GY6/6 (anthocyanin 2.5R4/6). Ventral side of internodes — 5GY6/6. Dorsal side of nodes — 5GY6/6. Ventral side of nodes — 5GY6/6.

*Internode length* (*upper mature sun cane*).—13.20 cm.

*Internode width* (*upper mature sun cane*).—6.7 mm.

*Node width*.—10.4 mm.

Bud:

*Bud description*.—Winter bud — very little and pointed, color 2.5YR4/6. Green bud — pointed, color 2.5GY6/8 with anthocyanin 5R3/6.

*Time of bud burst*.—February 25.

*Time of bud leaf burst*.—March 2.

Tendrils:

*Form*.—Mostly trifid.

*Size*.—Medium/long.

*Length*.—22 cm.

*Diameter*.—2.5 cm.

*Texture and distribution*.—Smooth, discontinuous, 00000011011011011 (0 means no tendril at that node and 1 means there is tendril at the node).

*Color*.—Mature — 4 weeks, 2.5GY7/8. Immature — 10 days, 2.5Y6/6.

*Anthocyanin*.—Mature — absent. Immature — present, 5YR4/4.

Growing tips (young shoot):

*Pubescence*.—Present, very high density of prostate hairs on the shoot tip.

*Color*.—2.5Y8/6.

*Anthocyanin*.—Absent.

*Shape*.—Wide open.

*Apex*.—Triangular.

*Form of tip*.—Wide open.

*Shoot attitude before tying*.—Semi-erect.

Leaves:

*Shape*.—Pentagonal.

*Density*.—Medium.

*Apex*.—Pointed.

*Base*.—Rounded.

*Number of lobes*.—3.

*Depth of upper lateral sinuses of mature leaves*.—Superficial.

*Arrangement of lobes of upper lateral sinuses on mature leaves*.—Open.

*Margin*.—Irregular teeth.

*Length of teeth on margin*.—2 to 10 mm.

*Shape of teeth on margin*.—Mixture of both sides straight and both sides convex.

*Texture* (*immature leaf*).—Upper surface — smooth, absent or very sparse density of erect hairs and low density of prostrate hairs between main veins on upper side of blade. Lower surface — smooth, absent or very sparse density of erect hairs and medium density of prostrate hairs between main veins on lower side of blade.

*Texture* (*mature leaf*).—Upper surface — smooth, low density of prostrate hairs between main veins on upper side of blade. Lower surface — smooth, medium density of prostrate hairs between main veins on lower side of blade.

*Size*.—Immature: Length — 8 cm, 10 days. Width — 7.5 cm, 10 days. Mature: Length — 18.6 cm, 4 weeks. Width — 17 cm, 4 weeks.

*Ratio of length/width of teeth* (*mature leaf*).—Medium.

*Color*.—Immature leaf: Upper surface — 5GY5/6. Lower surface — 2.5GY7/4. Mature leaf: Upper surface — 5GY4/8. Lower surface — 5GY7/4. Autumn coloration: Upper surface — 2.5Y8/6. Lower surface — 2.5Y8/6.

*Venation*.—Pattern — palmate (veins on upper leaf are flat; veins on lower leaf are raised), without anthocyanins coloration. Length of middle vein in mature leaves — 12 cm. Degree of Prostrated Hairs on Immature Leaf Lower Surface Main Veins — Dense. Degree of Prostrated Hairs on Immature Leaf Lower Surface Main Veins — Medium. Density of Erect Hairs on Mature Leaf Lower Surface Main Veins — Absent. Color: Upper surface — 2.5GY6/4. Lower surface — 5GY6/6.

*Petiolar sinus*.—Mostly slightly overlapped, V-shaped.

*Petiole*.—Length — 9.5 cm. Diameter — 2.85 mm. Color — 5GY7/6 (anthocyanin 5YR5/4).

Floral cluster:

*General description and location.*—Mostly 4th and 5th node; 10% without shoulders.

*Quantity of inflorescences per cluster.*—780.

*Size.*—Length — 20 cm. Width — 9.5 cm hanging; 15 cm shoulders spread.

*Peduncle.*—Length — 6.75 cm.

*Inflorescences.*—Hermaphroditic.

*Stamens.*—5 per flower, straight, 3 mm.

*Anthers.*—Small, non-descript.

*Date of bloom.*—Start 27 April; 50% — 3 May, 100% — 6 May.

*Pollen amount.*—Sparse.

*Calyptra.*—5 segments, complete separation.

*Calyptra color.*—5GY4/8.

Fruit:

*Time of year of commercial harvest and shipment.*—Early season, July 20, in Murcia, Spain.

*Time of beginning of berry ripening.*—Early.

*Keeping quality.*—After 30 days of refrigerated conservation, the main and secondary stem remain hydrated, but the pedicel shows symptoms of dehydration. The berries keep its excellent flavor and crispness.

*Cluster* (*primary bunches*).—General size — big, 580 g. Length (without peduncle) — 21.8 cm. Width — hanging 12 cm; shoulders spread 20.4 cm. Density — medium. Peduncle length — 5.7 cm. Peduncle diameter — 3.18 mm. Peduncle color — 2.5 GY 7/6. Number of berries per cluster — 80 tipped; 90 not tipped.

*Berry.*—Size — large, 6.5 g. Diameter — 19.85 mm. Length — 26 mm. Shape — broad ellipsoid. Uniformity — very uniform. Brix content — 20.7° Brix. Titratable acidity — 0.465. Skin color (without bloom) — 2.5 GY 7/8. Skin color (with bloom) — 2.5GY 7/6.

*Pedicel.*—Length — 5 mm. Diameter — 1 mm. Color — 2.5 GY 5/8. Strength of attachment to berry — very strong.

*Cluster* (*secondary bunches*).—General size — small, 112.2 g. Length (without peduncle) — 10.5 cm. Width — hanging 5.5 cm; 7.5 cm shoulders spread. Density — medium. Peduncle: Length — 5.25 cm. Diameter — 2.92 mm. Color — 5 GY 7/6.

*Number of berries per cluster.*—20 berries.

*Berry.*—Size — medium, 4.7 g. Diameter — 17.7 mm. Length — 22.1 mm. Shape — broad ellipsoid. Uniformity — very uniform. Brix content — 21.8° Brix. Titratable acidity — 0.44. Skin color (without bloom): 2.5 GY 7/8. Skin color (with bloom) — 2.5GY 7/6. Pedicel: Length — 7 mm. Diameter — 1.2 mm. Color — 5 GY 7/8. Strength of attachment to berry-very strong.

Berry flesh:

*Color.*—2.5 GY 8/6.

*Anthocyanin coloration.*—Absent.

*Juice, color.*—2.5 GY 8/6.

*Juice production.*—Very high, 51.6%.

*Thickness of skin.*—Medium.

*Flavor.*—Intense, unique labrusca-toffee like, with hints of papaya and pineapple.

*Fragrance.*—Very intense, labrusca aroma, high geraniol.

*Texture.*—Crunchy.

*Firmness.*—Very firm.

*Seeds.*—Rudimentary, color 2.5 GY 5/4, length 3 mm and width 2 mm, two seeds per berry.

*Use.*—Table grape.

Disease and insect resistance: This cultivar is susceptible to the main diseases of its species, such as *Erysiphe necator, Plasmopara viticola, Botrytis cinerea, Daktulosphaira vitifoliae, Ceratitis capitata, Planococcus ficus, Planococcus citri, Empoasca vitis.*

What is claimed is:

1. A new and distinct variety of grapevine plant named 'BLOMG01' as substantially described and illustrated herein.

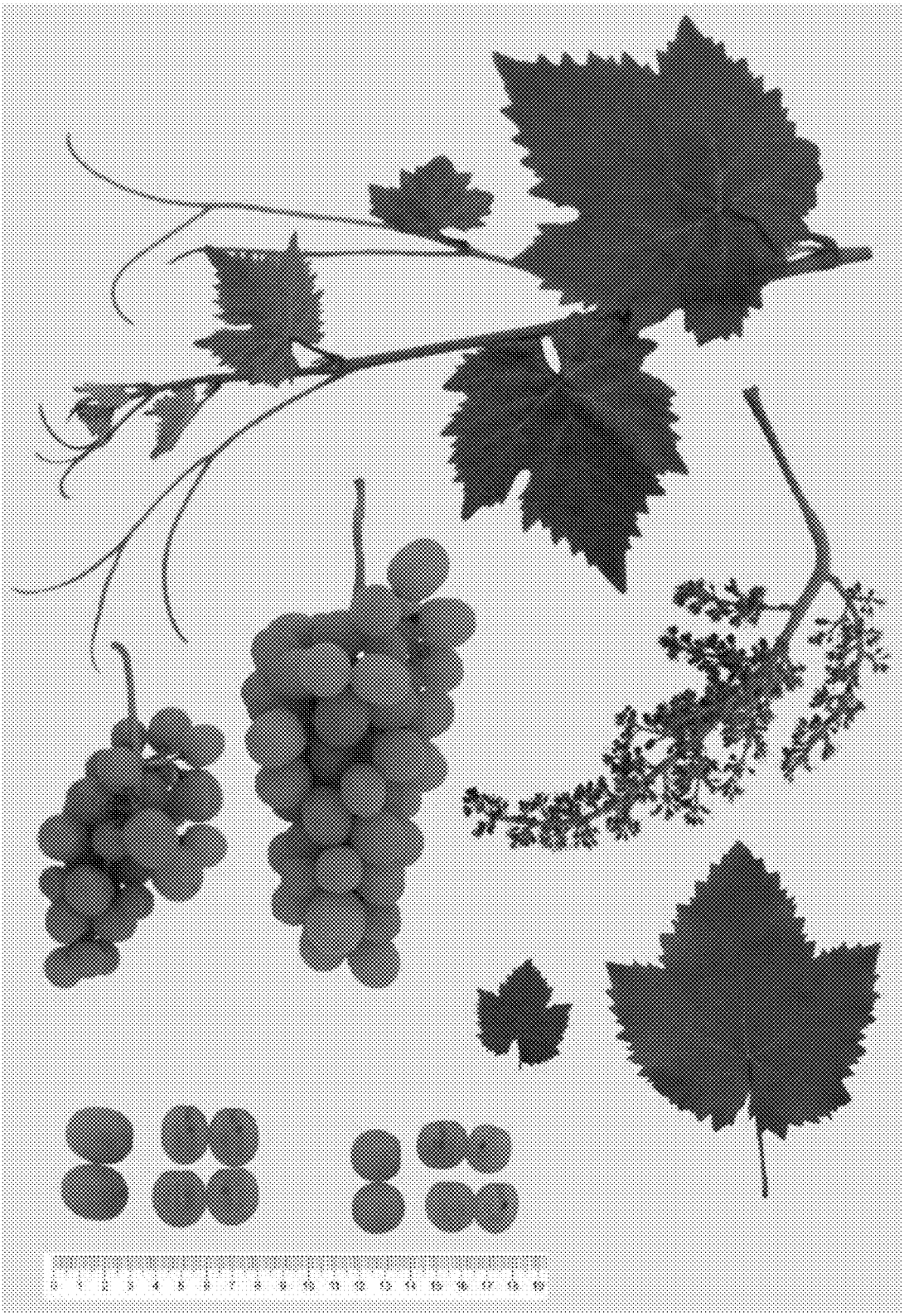

* * * * *